(12) United States Patent
Lindermeir et al.

(10) Patent No.: US 6,271,522 B1
(45) Date of Patent: Aug. 7, 2001

(54) PROCESS FOR THE QUANTITATIVE ANALYSIS OF GAS VOLUMES, SPECIFICALLY EXHAUST AND WASTE GASES FROM COMBUSTION SYSTEMS OR INCINERATION PLANTS, AS WELL AS SYSTEMS FOR PERFORMING THESE PROCESSES

(75) Inventors: Erwin Lindermeir, Munich; Peter Haschberger, Gauting; Birger Schimpp, Gilching; Franz Schreier, Planegg; Volker Tank, Eching, all of (DE)

(73) Assignee: Deutsches Zentrum fur Luft-und Raumfahrt E.V., Bonn (DE)

( * ) Notice: Subject to any disclaimer, the term of this patent is extended or adjusted under 35 U.S.C. 154(b) by 0 days.

(21) Appl. No.: 09/312,058

(22) Filed: May 17, 1999

(30) Foreign Application Priority Data

May 16, 1998 (DE) .............................. 198 21 956

(51) Int. Cl.$^7$ ....................................... G01J 3/02
(52) U.S. Cl. ................... 250/341.1; 250/338.5; 250/341.3
(58) Field of Search ................. 250/341.1, 338.1, 250/338.5, 343, 352, 373, 341.3

(56) References Cited

U.S. PATENT DOCUMENTS

| | | |
|---|---|---|
| 4,569,592 | 2/1986 | Osada et al. . |
| 4,790,652 | 12/1988 | Uneus et al. . |
| 5,319,199 * | 6/1994 | Stedman et al. ................. 250/338.5 |
| 5,551,780 | 9/1996 | Wintrich et al. . |
| 5,724,135 | 3/1998 | Bernhardt . |
| 5,726,450 * | 3/1998 | Peterson et al. ................. 250/338.5 |
| 5,831,267 * | 11/1998 | Jack et al. ........................ 250/338.5 |

FOREIGN PATENT DOCUMENTS

| | | |
|---|---|---|
| 4324118 | 1/1995 | (DE) . |
| 9118280 | 11/1991 | (WO) . |

OTHER PUBLICATIONS

Hilton et al., "Quantitative analysis of remote gas temperature and concentrations from their infrared emission spectra", *Meas. Sci. Technol.*, vol. 6, pp. 1236–1241, (1995).

Debal et al., "A simple experimental system for the determiniation of spatial spectroscopic optical emission" *Meas. Sci. Technol.*, vol. 8, pp.618–622, (1997).

Zhang et al., "Determination of the Temperature Profile of Axisymmetric Combustion–Gas Flow from Infrared Spectral Measurements", *Combustion and Flame*, vol. 65, No. 2, pp. 163–176, (1986).

Patent Abstract of Japan, Pub. No. 08005547, Pub. date Jan. 12, 1996.

* cited by examiner

*Primary Examiner*—Constantine Hannaher
*Assistant Examiner*—Otilia Gabor
(74) *Attorney, Agent, or Firm*—Browdy & Neimark (57) ABSTRACT

For quantitative analysis of gas volumes, specifically combustion exhaust gases, by means of emission or absorption spectrometry in the ultraviolet, visible and infrared spectral range, geometrically defined and reproducibly adjustable observation planes are oriented perpendicular to the longitudinal axis of an exhaust stream. In a first series of measurements a number of m spectral measurements is performed, in such a way that the optical axis of a spectrometer is always located in the respective observation level but is shifted in a parallel direction by a first distance from one measurement to the next. In a second series of measurements n measurements are performed, in such a way that the optical axis is again located in the observation plane and is shifted in a parallel direction by a second distance from each measurement to the next. The (m+n) measurements produce two orthogonal sets of line of sights, which form a grid with (m·n) intersecting volumes. With the aid of the (m+n) measurements, each measurement yields the spectral transmission τ(v), or the spectral radiation intensity I(v) which is integrated via the total gas volume in the beam of rays of the spectrometer field of view.

24 Claims, 6 Drawing Sheets

Lines of Sight of the spectrometer

PROCESS FOR THE QUANTITATIVE ANALYSIS OF GAS VOLUMES, SPECIFICALLY EXHAUST AND WASTE GASES FROM COMBUSTION SYSTEMS OR INCINERATION PLANTS, AS WELL AS SYSTEMS FOR PERFORMING THESE PROCESSES

FIELD OF THE INVENTION

The present invention relates to processes for the quantitative analysis of gas volumes, more specifically random exhaust gases from combustion systems, such as jet engines, their combustion chambers and other gas turbines, as well as from incineration plants, chemical facilities, power plant furnaces, or landfills. The invention also relates to systems for performing these processes, and to modeling processes and evaluation processes.

REVIEW OF RELATED TECHNOLOGY

Nowadays the characteristics of industrial incineration plants or combustion systems, which include aircraft turbines and similar combustion systems, are determined by (among other factors) two essential requirements: the maximization of the energetic effectiveness of the combustion (an economic requirement) and the minimization of undesirable components in the exhaust gas (an ecological requirement). Ecological aspects also determine, among other things, the interest in the quantitative composition of exhaust gases that occur in natural fires. The fact that combustion processes, as a rule, do not proceed in a spatially homogeneous form, and that the degree of effectiveness of combustion and the composition of the exhaust gases are impacted by inhomogeneities, make a spatially resolved analysis of the combustion and exhaust gas desirable.

The operational part of gas analysis is currently performed by sampling. This encompasses both static collection processes, such as the collection of individual samples, for example by means of evacuated collection containers, and also dynamic collection processes, e.g., continuous sampling, for example by means of extraction systems. A continuous, spatially resolved exhaust gas analysis for the usually large exhaust streams from the systems in question is not possible with these methods, or else is possible only with technically highly complex and/or time-consuming processes.

There furthermore is no a priori guarantee that the sample does not undergo any changes during the time between collection and analysis, for example due to temperature changes and/or chemical reactions. The analysis, as a rule, requires different methods for the different components of the exhaust gas and is frequently time-consuming. The probes used in the sampling process may cause undesired reactions with the combustion process, possibly even jeopardizing the operation of the system, for example, in the case of combustion chambers or jet turbine engines.

In recent times, the suitability of non-intrusive infrared-spectrometric processes for emission analysis has been studied within the context of research projects. These optical processes do detect several components of the exhaust gas simultaneously. However, the information along an optical beam line is integrated over the volume scanned. These processes therefore do not permit a spatial resolution, as is required particularly for the analysis of exhaust gases from gas turbines under development; instead they offer only one dimensional detection of the exhaust gases.

The following are shortcomings of the methods currently used for exhaust gas analysis:

1. Processes in which samples are collected are slow; they require a separate analysis instrument for each component of the exhaust gas; they involve the risk that samples may become corrupted; if they permit a high spatial resolution they are technically highly involved and/or require considerable amounts of time; and they may cause problems in the combustion process.

2. Non-intrusive infrared spectrometric methods permit only a one-dimensional detection of the exhaust gases and yield the concentrations of the exhaust gas components in the volume of the covered beam of rays only as a mean value. Particularly for the development of combustion chambers and turbines of jet engines, however, it is necessary to know the spatially resolved distribution of the temperature and concentration of the exhaust gas constituents, in order to be able to make any statements regarding the effectiveness and the emission indices (quantity of exhaust gas relative to the burnt amount of fuel). A knowledge of the spatial distribution could also be used to derive characteristics of and, hence, development criteria for the combustion chamber.

3. The spatial resolution of the measurement, which is required for the precise quantitative determination of quantities of exhaust gas from industrial or natural combustion processes, is not possible in a non-intrusive manner and often cannot be justified because of the required expenditures.

Essential elements of the evaluation comprise a modeling of the infrared radiation received by a detector by solving the radiation transport equation and fit the model to the measured by parameter estimation methods.

Figure 1:
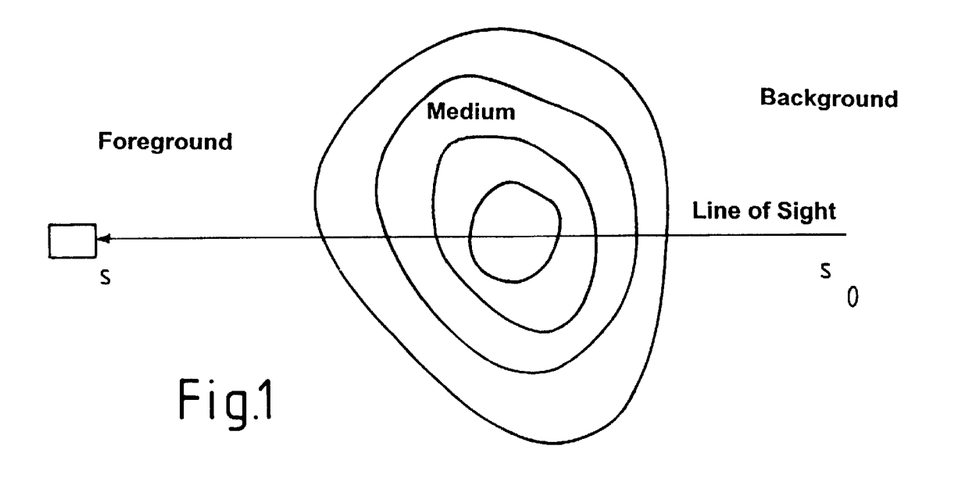
FIG. 1 is a schematic representation of the geometry of the radiation transport calculation through a medium.

In a forward model of radiation transport, the radiance (intensity) I(v, s) of wave-number v which is received by a detector at a location s is obtained with the integral form of the radiative transfer equation:

$$I(v, s) = I(v, s_0)\mathcal{T}(v; s, s_0) + \int_{s_0}^{s} ds' B(v, T(s')) \frac{\partial \mathcal{T}(v; s, s')}{\partial s'} \quad (1)$$

wherein s' denotes the distance from the observer along the line of sight (see FIG. 1); B denotes the Planck function at the temperature T, and I(v, so) denotes a source term. The monochromatic transmission $\tau(v; s,s')$ describes the attenuation of the radiation between two locations $s_0$ and $s_1$ and is defined by:

$$\mathcal{T}(v; s_0, s_1) = \exp\left(-\int_{s_0}^{s_1} k(v, s') n(s') ds'\right), \quad (2)$$

wherein k(v;s)=k(v,p(s),T(s)) is the pressure-dependent and temperature-dependent absorption coefficient, and n(s) is the molecular particle density. In inhomogeneous media these values are spatially dependent. In the common radiative transfer models, the path integration of equations (1) and (2) are performed via the so-called Curtis-Godson approximation in such a way that the inhomogeneous medium is replaced by a series of homogenous layers with constant temperature and molecule concentrations, for example the mean values within these layers, and summed over these layers.

In the general case with a number of absorbing molecules, k(v;s')n(s') must be generalized via a sum over all species $$\Sigma_g k_g(v;s') n_g(s')$$

The radiation received by a spectrometer must, of course, be calculated via convolution of the monochromatic spectrum (equation (1) or (2)) with the instrumental line shape function.

The shortcoming of this modeling of the measured spectrum, as it is used in the customary evaluation processes, is that the finite aperture and the finite field of view (FOV) of real spectrometers are not taken into consideration. Furthermore, the Curtis-Godson approximation, which is "commonly" used for radiative transfer calculations, should not be used here since least squares methods, as will be explained later, generally require a considerably greater number of iteration steps than solving the integrals with standard quadrature methods.

The equations (1) and (2) are (generally non-linear) integral equations of the general form $g(v)=\int Y[v,f(s)]ds$, which are converted into a linear equation system for the inversion, i.e., the determination of the unknown "source function" f (e.g., the temperature or gas concentration profile) via linearization—which leads to the Fredholm integral equation of the first type, $g(v)=\int K(v,s)f(s)ds$, and—discretization. As a general rule, a spectrum is known only for a finite number of discrete spectral elements $v_i$, $i=1, \ldots, m$. In the customary evaluation processes the unknown temperature and/or gas concentration profiles are described only through their mean values, i.e., constant profiles are assumed within the exhaust stream, for example a one-layer model of the gas volume or a three-layer model when foreground and background are taken into account.

If the number of measured points m is greater than the number n of unknown values, the discretization of the radiative transfer equation (1) or equation (2) yields an over-determined equation system. The customary approach is, therefore, a solution through minimization, $$\min_{x}\|g - y(x)\|^2 = \min_{x}\sum_{i=1}^{m}(g_i - y(v_i, x))^2. \quad (3)$$

wherein $g=(g_1, \ldots g_m)=(g(v_1), \ldots, g(v_m))$ is the measured (transmission or emission) spectrum and the m-vector y describes the modeled spectrum, which, as a general rule, has a non-linear functional correlation with the unknown mean values for the temperature and gas concentrations (represented here by the n-vector x), as well as with the wave number v according to equation (1) or (2).

Equation (3) is a non-linear least squares problem for the unknown n-dimensional vector x, which is solved by iteration, such as the Gauss-Newton or Levenberg-Marquardt methods.

A shortcoming of these customary processes lies in the highly simplified presentation of the unknown temperature and/or concentration profile in the gas volume. Furthermore, it must be assumed that the extent of the layer is known.

OBJECTS AND SUMMARY OF THE INVENTION

It is therefore an object of the invention to create analysis processes for exhaust gases from combustion processes, which permit non-intrusive measurements, operate quickly, detect many exhaust gas components and their temperatures simultaneously, and encompass a determination of their spatial distribution. It is furthermore an object of the invention to describe systems with which to perform these processes, as well as improved modeling and evaluation processes.

The processes according to the invention for the quantitative analysis of exhaust gas employ a three dimensional, computer-assisted model of the exhaust gas phenomenon, namely the exhaust stream from a combustion chamber, gas turbine or rocket, an exhaust gas column in a smoke-stack, an exhaust plume from a volcano or smoke-stack, etc. Furthermore, to perform the exhaust gas analysis processes according to the invention, a spectrometric measuring system is used, in which the ultraviolet, visible or infrared radiation is detected in the exhaust gas from different directions. Furthermore, an evaluation method is used in accordance with the invention, in the form of a one dimensional multi-dimensional inversion process.

With the exhaust gas analyzers that are provided according to the invention, a spectrometer is used as the measuring instrument, which preferably operates in the infrared spectral range, but may also be optimized for the ultraviolet or visible spectral range, depending on the requirements at hand. In the process the spectrometer is operated in a known manner as an emission spectrometer, i.e. in a fully passive mode; which means it receives the radiation emitted by the waste gases, which will generally be an infrared radiation, but which, in the case of high exhaust gas temperatures such as from rocket engines, may also be visible or ultraviolet radiation.

The spectrometer may also be operated, in a known manner, as an absorption spectrometer, i.e. , it is operated in an active set-up in combination with a radiation source in such a way that the measured volume of the exhaust gas is located between the radiation source and the spectrometer and is traversed by the radiation, which is partially absorbed before it is received by the spectrometer.

For an absorption set-up, broad-band radiation sources are used in the ultraviolet, visible and preferably infrared spectral range, for example black-body radiation emitters or Globar radiation emitters, which are adjusted to the actively radiating spectral ranges of the gases to be examined. However, small-band radiation sources, such as lasers and laser diodes, are usable as well. Any known type of spectrometer may be used, as long as it is suitable for application in rough environments, such as on jet engine test stands.

Particularly suitable are Fourier spectrometers of the Michelson type, particularly if they have a robust design, for example the MIROR Michelson interferometer that uses a rotating retroreflector, or a similar model. The Michelson interferometer combines large spectral bandwidths with a high spectral detection rate (low noise equivalent radiant intensity, or NESR).

The required spectrometer resolution should generally correspond to the natural line width of the measured gases, which is approximately $\Delta v=0.1$ cm$^{-1}$ or better at the ambient pressure on the earth's surface; however it can be adjusted to the specific requirements of the observed spectral range. It may be necessary, for example, to realize a higher spectral resolution, if the lines of different present gases are located close together and must be separated to reduce or prevent interactions. A lower spectral resolution may be sufficient if the lines of a gas are spaced far apart and no lines from other gases interfere.

The processes according to the invention are of particular importance with combustion processes or thermal reactions during which exhaust gases are released, both in industrial processes, as well as in nature (volcanos, forest fires, etc.). The process according to the invention may be used to evaluate exhaust gases stemming from any random solid, liquid or gaseous fuels. The exhaust gas analysis relates to the detection, classification and quantification of the gases contained in the observed volume, as well as of nonburned fuel particles, such as hydrocarbons and solid particles, like soot, and it also relates to the determination of the temperature of the gases and other components.

The term exhaust gases as it is used below shall explicitly include all other gases, although testing of exhaust gases is currently viewed as the most important application.

In the process of the present invention, the optical axis of a system is geometrically defined and reproducibly adjustable relative to the exhaust gas in such a way that observation planes through the exhaust gas can be defined. These observation planes are given based on a number of m spectral measurements being performed with the system in a first series of measurements during which the optical axis of the spectrometer always lies in the observation plane but is shifted in a parallel direction by a distance $s_x$ from one measurement to the next. In a second series of measurements, n measurements are performed during which the optical axis again lies in the observation plane, however this time perpendicular to the direction of the axis of the first process step. During this series of measurements the optical axis is shifted in a parallel direction by a distance $s_y$ from one measurement to the next.

The parameters m, n, $s_x$, $s_y$ are dependent upon the geometry of the exhaust gas volume and the size of the field of view of the spectrometer. In special cases it may be that m=n and $s_x=s_y$. The distances $s_x$ and $s_y$ are selected so that they are equal to the diameter of the spectrometer field of view at the location of the measurement so that parallel line of sights do not have any distance from one another. (The "line of sight" of the spectrometer would correspond to the field of view of a telescope.) However, they may also be smaller, in which case the parallel line of sights overlap, or they may be larger, in which case the parallel line of sights do have distances from one another. In this manner a set of (m+n) measurements is obtained.

Depending on the applied process, each measurement yields the spectral transmission $\tau(v)$, wherein v represents the wave number (in units of $cm^{-1}$), i.e., the inverse wavelength of the radiation. It may also yield the spectral radiance or intensity I(v), which is integrated over the beam of rays of the spectrometer field of view over the total gas volume.

Based on the arrangement of the optical axis in the observation plane, two orthogonal sets of line of sights are obtained during the measurements, which form a grid with (m·n) intersecting volumes. The size of these volumes is given by the geometry of the arrangement, such as the solid angle of the spectrometer, and the distance to the intersecting volume. Each intersecting volume is captured spectrometrically from two directions, which are orthogonal to one another. Here and in the following claims, these intersecting volumes are denoted as "partial volumes".

The integral measurement via each of the m line of sights of the first series of measurements contains n volumes, each of which corresponds to a volume in the n beams of rays of the second measurement series. The same also holds true the other way around: the integral measurement via each of the n line of sights of the second series of measurements contains m volumes, each of which corresponds to a volume in each of the m beams of rays of the orthogonal first series of measurements. The planar set-up of the measurement system permits the establishment of additional observation planes through the exhaust gas by the above method, to obtain additional data sets in the same manner, through spectral measurements. The exhaust gas is thus detected in the three spatial dimensions.

Besides the measurement strategy with optical axes that are shifted in a parallel direction, and orthogonal measurement series, another measurement geometry may also be selected. For example the measurement series may also be designed with fanned optical axes of the line of sights, and more than two measurement series (fans) may be included as well. These (non-orthogonal) fans are located in one and the same observation plane. Here again, intersecting volumes are created, which are captured from two or more observation directions and determined geometrically as earlier described.

The (two-, three- or) multi-dimensional evaluation processes according to the present invention for the analysis of exhaust gases employ both the above-described model of the exhaust gas phenomenon, as well as the data sets obtained by the measurement. A goal of the present invention is to match the measured data and an analytical description of the measured data (the result of the model calculation), to obtain the required parameters (gas concentrations, temperature, possibly pressure). To this extent the evaluation processes form a spatial matrix of gas volumes, whose geometric dimensions (extent and arrangement in space) are determined by the geometry of the measurements and by the spectrometer field of view.

In the so-called forward calculation, the spectral radiance or the spectral absorption are calculated for each visual beam. For this purpose estimated values are assumed for the gas concentrations, the temperatures, and possibly also for the pressure, and for each line of sight these are combined into a model-derived value of the radiative transfer characteristics of each gas volume in the line of sight. In the retrieval process, the modeled measurements are compared to the actual measured values and the estimated values of the sought model parameters (gas concentrations, temperatures, pressure) are iteratively improved until an optimum match has been reached, which is defined by a convergence criterion.

The parameters found in this manner represent a mean value for each volume element, which means that the desired spatially resolved analysis has been attained. This analysis is made possible by the orthogonal (or otherwise structured) measurement geometry and the (two-, three- or) multi-dimensional evaluation process. In this context it is particularly advantageous that each studied measurement volume is processed in the evaluation process in a twofold (orthogonal) or manyfold (multidimensional) measurement observation.

An additional relation or parameterization of the measurement volumes of a two-, three- or multi-dimensional measurement in the evaluation process becomes possible in the case of directed and structured exhaust streams. These are present within smoke stacks and in the case of jet engines and gas turbines in the vicinity of the nozzle. Here, analytical relations between the gas concentrations and the temperatures are present both perpendicular to the gas flow, as well as in the direction of the flow, which can be utilized in the evaluation process. Exhaust gas conditions like these are particularly well suited for the analysis process.

BRIEF DESCRIPTION OF THE DRAWING FIGURE

Information regarding the dimensioning of a spectrometer for the exhaust gas analysis will be presented below, with reference to the appended drawings, wherein.

DETAILED DESCRIPTION OF THE PREFERRED EMBODIMENTS

Figure 2:
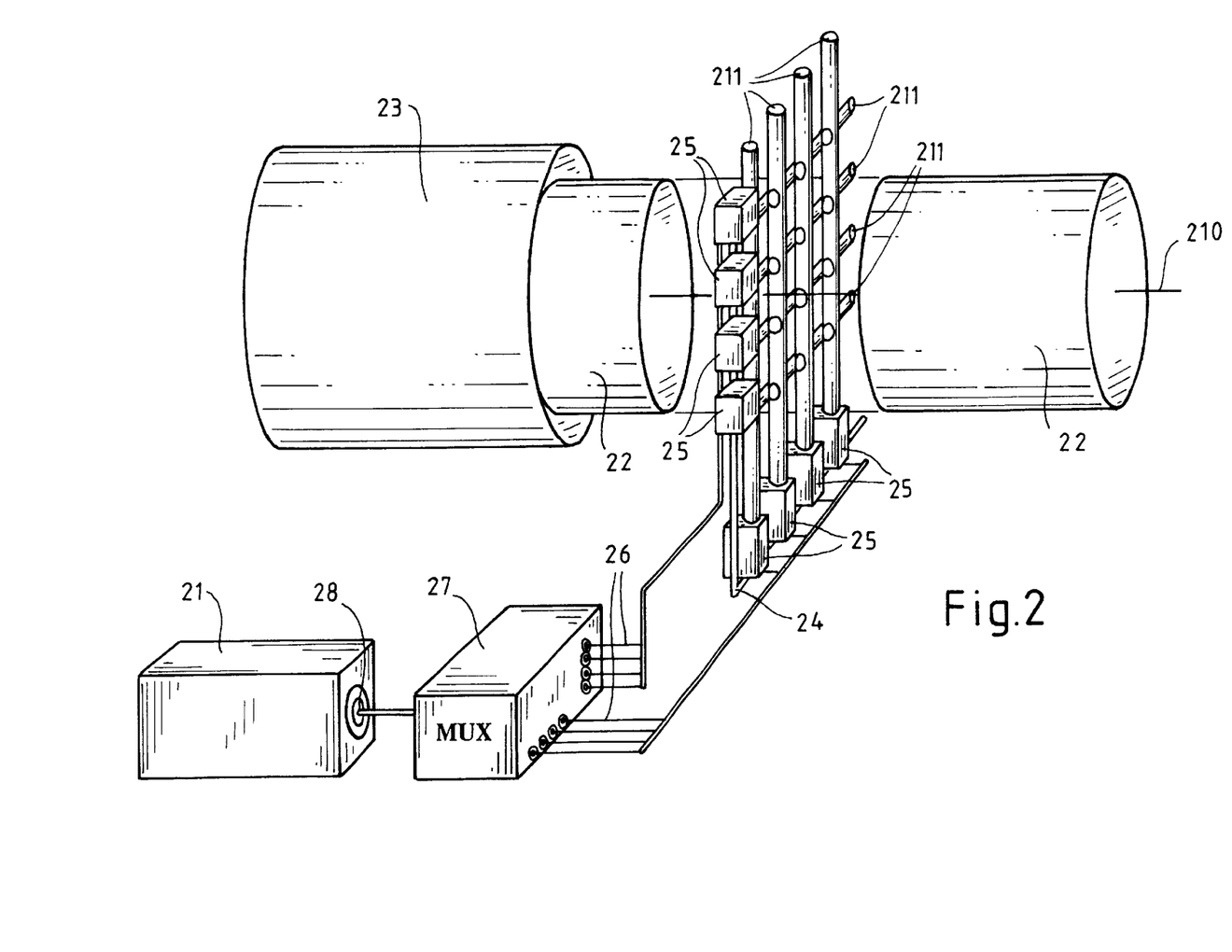
FIG. 2 is a schematic representation of a spectrometric measuring set-up at the exhaust stream of an aircraft engine on the test stand and a multi-dimensional radiation detection.

FIG. 2 shows a measuring set-up with a spectrometer 21 at a certain distance from a measured object, which in FIG. 2 is an exhaust stream 22 of an aircraft engine 23. The exhaust stream 22 is encompassed concentrically by a holding device 24 illustrated only schematically in FIG. 2, which is mounted in a manner not shown in the drawing so that it can be shifted in a direction parallel to itself and concentric (parallel) to the longitudinal axis 210 of the exhaust stream 22.

Mounted on the holding device 24 are a number (m+n) of optical receiver units 25, comprising known lens or mirror systems not shown in the drawing. Coupled to each of the (m+n) receiver units 25 is a fiber optics bundle 26, whose respective other end connects to an input of an optical multiplexer 27. The optical multiplexer 27 is coupled with its optical output to the optical input 28 of the spectrometer 21.

The fiber optics bundles used in the process may be quartz fiber bundles in the visible and near infrared spectral range, or heavy-metal fluoride glasses in the range of 3 μm to 5 μm, as well as other glasses that are available for this and other spectral ranges. The optical system, which comprises receiver units 25, fiber optics bundles 26, multiplexers 27, and spectrometers 21, is dimensioned so that the receiver units 25 have a visual field angle with a small divergence (a few mrad to several degrees). In dependence upon the geometric extent of the measured object, the visual field angle is dimensioned in such a way that the radiation is received from preferably parallel beams of rays 211 (e.g., beams of rays with a small divergence) that do not overlap or overlap only to a small degree, as illustrated in the example of FIG. 2.

The (m+n) receiver units 25 are arranged and adjusted to one another inside the holding device 24 in a plane that is perpendicular to the longitudinal axis 210 of the exhaust stream 22 in such a-way that optical axes of the beams of rays 211 received by the m receiver units 25 that are oriented parallel to one another are oriented perpendicular to the axes of the beams of rays that are received by the n receiver units 25, that also oriented parallel to each other. The optical axes of the (m+n) receiver units 25 thus span a grid, which is formed of orthogonal beams of rays located perpendicular to the axis 211 of the exhaust stream 22. In FIG. 2, m=n=4 was chosen for a simplified illustration.

During the measuring data acquisition (with the engine running) the hot exhaust gases of the engine emit an infrared radiation, which is measured by the (m+n) receiver units 25 and transmitted via the fiber optics bundles 26 to the multiplexer 27. During this process each receiver unit 25 measures only the radiation from its corresponding beam of rays 211. The multiplexer 27 transmits the radiation from all fiber bundles sequentially to the spectrometer 28, where the corresponding spectrum is determined, i.e., (m+n) spectra are determined for each measured position along the longitudinal axis of the exhaust stream 22.

These raw spectra are converted into calibrated radiance spectra (intensity) or absorption spectra. These spectra contain spectral information from the entire corresponding beam of rays or line of sights 211. This information, contained in the individual bundles, is interrelated via the grid. Each of the (m+n) beams of rays has a corresponding gas volume, whose radiation is integrated in its entirety and recorded. Each beam can be further divided into m or n partial volumes along its beam axis. If it is one of the m beams it will have n partial volumes along its length; if it is one of the n beams it will have m partial volumes along its length. Each partial volume provides a (partial) radiation contribution to each of the m beams and also to each of the n beams. The evaluation process of the present invention links the beam information in the manner explained below.

Figure 3:
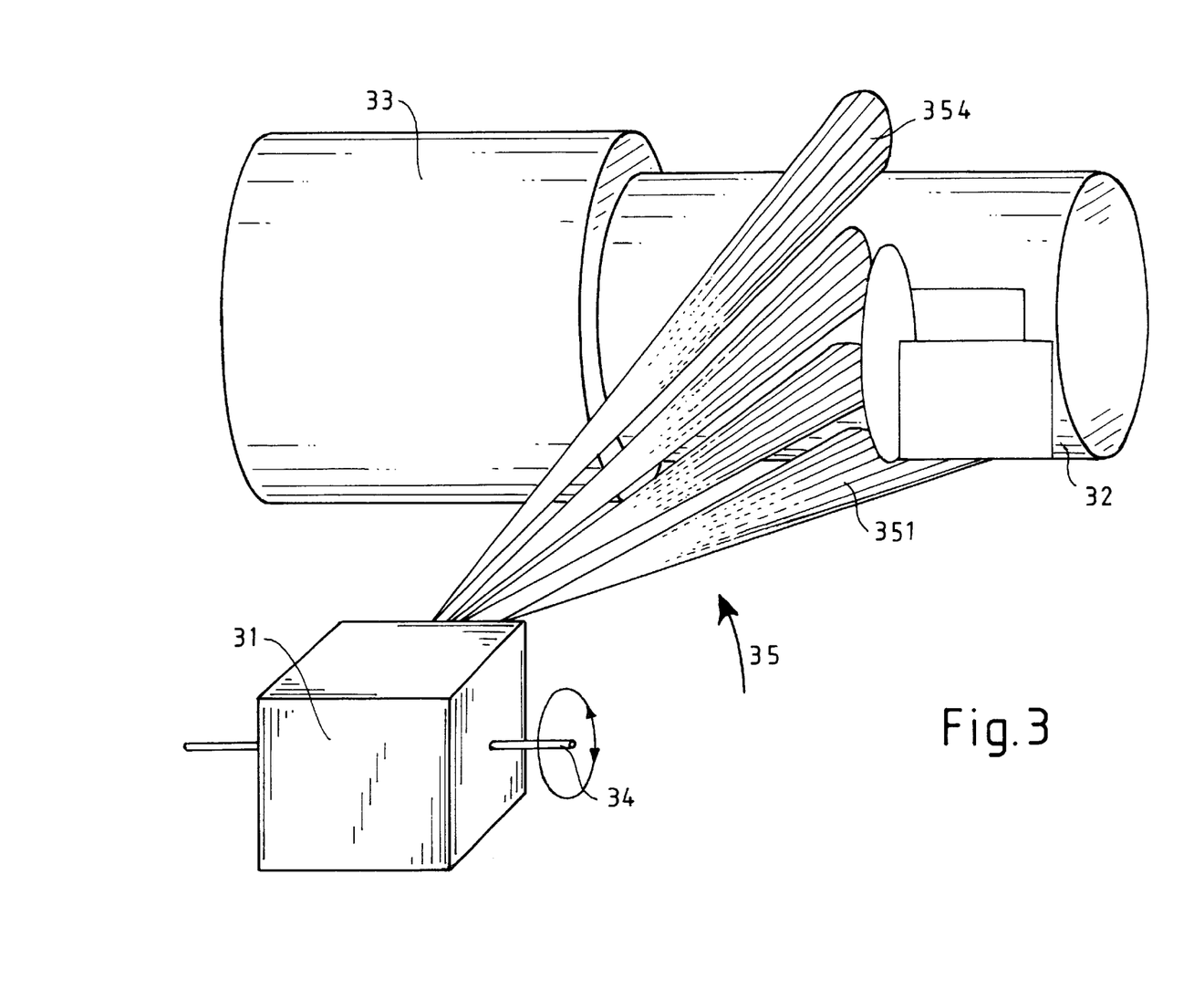
FIG. 3 is a schematic representation of a spectrometric measuring set-up at the exhaust stream of an aircraft engine on the test stand and a multi-dimensional radiation detection.

FIG. 3 shows a measuring set-up in spectrometer 31 at a certain distance from a measured object, specifically an exhaust stream 32 of an airplane engine 33. The spectrometer 31 can be swivelled around a rotation axis 34 and can be locked in fixed angle positions. In this manner the visual beams 35 are guided in different directions. In FIG. 3 in the directions are 351 to 354. The swivelling movements and the grid can be adapted to the measuring requirement at hand, i.e., it can be fanned narrower or wider, in such a way that the line of sights 35 can overlap one another, follow one another without gaps or have gaps of adjustable widths; their number is variable as well.

Figure 4A:
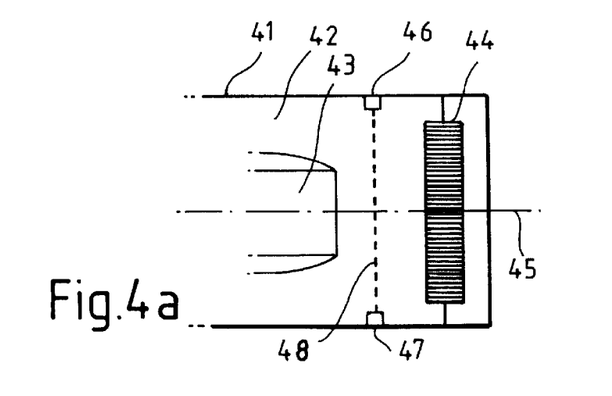
FIG. 4a and 4b represent a longitudinal section and a cross-section through a measuring set-up for in-flight measurements inside jet engines or inside gas turbines during their operation.
Figure 4B:
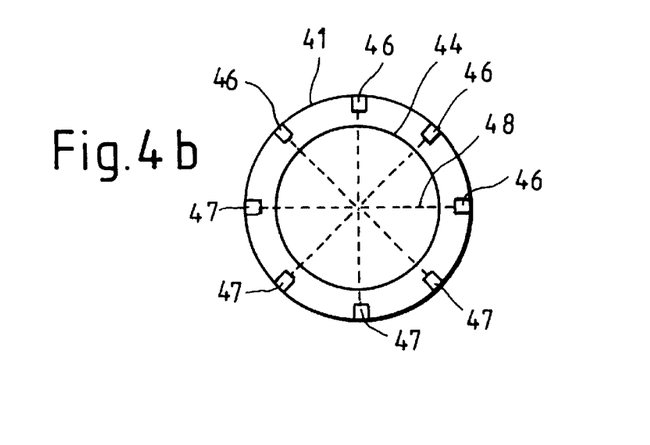

FIG. 4 shows a measuring set-up which is used for in-flight measurements inside jet engines or inside gas turbines during their operation; this is a preferred embodiment of a measuring system according to the invention which is installed permanently inside a jet engine or gas turbine. A jet engine 4 (gas turbine), indicated only schematically, has a housing (an outer encasing) 41, a bypass (cold gas) 42, a hot gas nozzle 43, and a mixer 44. The measuring system comprises radiation transmitters 46 (for example black-body radiation emitters or light-emitting diodes), and devices 47 to receive radiation (for example receiver optics for coupling into optical fibers, radiation detectors, or the like). The devices 47 are mounted radially symmetrical and are arranged equidistant along the inner circumference of the housing 41 in such a way that the transmitters 46 are located opposite receivers 47 in pairs and radiation travels along a line of sight 48 from the transmitter 46 to the receiver 47. These lines of sight 48 extend radially to the exhaust stream 45.

In an embodiment not shown in the drawing the lines of sight of the transmitter 46 and the receiver 47 are not oriented radially to the exhaust stream but form measuring distances that are parallel to one another and aligned perpendicular on the longitudinal axis of the exhaust stream 45. The central pair consisting of a transmitter 46 and a receiver unit 47 thereby forms the longest measuring distance, which is equal to the inside diameter of the housing 41; the measuring distances of the subsequent pairs, which are parallel to the former, increasingly decrease in length from the center to the outside.

The above two set-ups for measurements inside a jet engine (a gas turbine) are shown in a mode of operation for absorption measurements. In another preferred mode of operation they are also operated as emission measuring systems. For this purpose the transmitters 46 are switched off or removed. The receivers 47 then receive the radiation from the gas layers in the bypass 42 and in the hot gas 43.

In both modes of operation measurements are performed as reference measurements when the jet engine (gas turbine) is turned off, and as operating measurements when the jet engine is running.

The simulation and evaluation of the invention are adapted to the above described measuring systems of the invention. The simulation permits the calculation of the radiation characteristics (spectral radiance, radiation transfer, spectral emission and absorption) of the gas according to the gas parameters, such as the particular emission components, as a function of their spatial density distribution and temperature in each volume unit or volume cell of the exhaust gas. The simulation also calculates the radiation transfer, through all gas volumes, to a spectrometer. In the process the simulation also models gas layers in the line of vision of the spectrometer (foreground, background) that are not part of the exhaust gas. The solid and gaseous components contained in the exhaust gas are advantageously derived, in a known manner, from the type of fuel burnt and the combustion process.

For calculation of the radiation characteristics of the exhaust gas components, the known molecular spectroscopic parameters of the relevant gases are used: spectral line position, spectrum line strength, spectral line width, etc. These parameters are stored in computer-readable databases, such as HITRAN and the like. If gases are to be examined whose spectroscopic parameters are not yet known, these must be determined by known methods in laboratory measurements, after which they can be used in the invention. The model is used both for estimating the radiation characteristics of various random exhaust gas mixtures, as well as in the evaluation process of the invention, as will be shown later.

Figure 5:
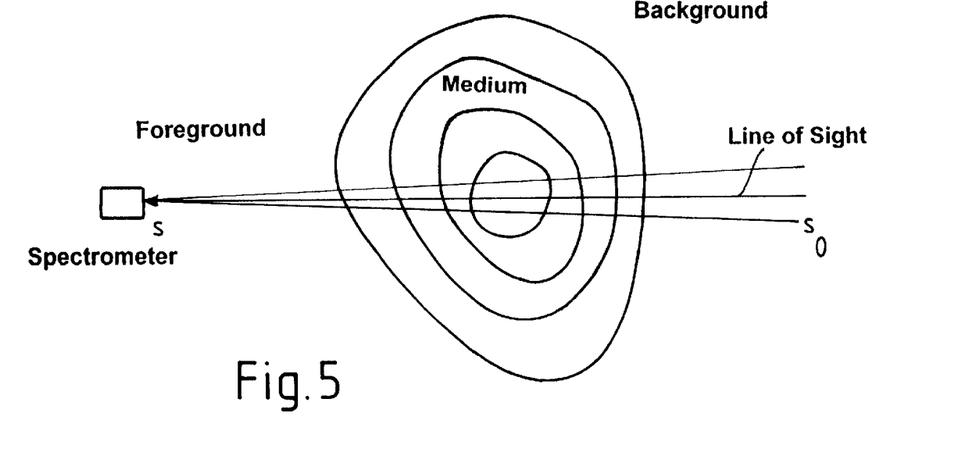
FIG. 5 is a schematic illustration of the geometry of the radiation transport at a finite FOV of the spectrometer.
Figure 6:
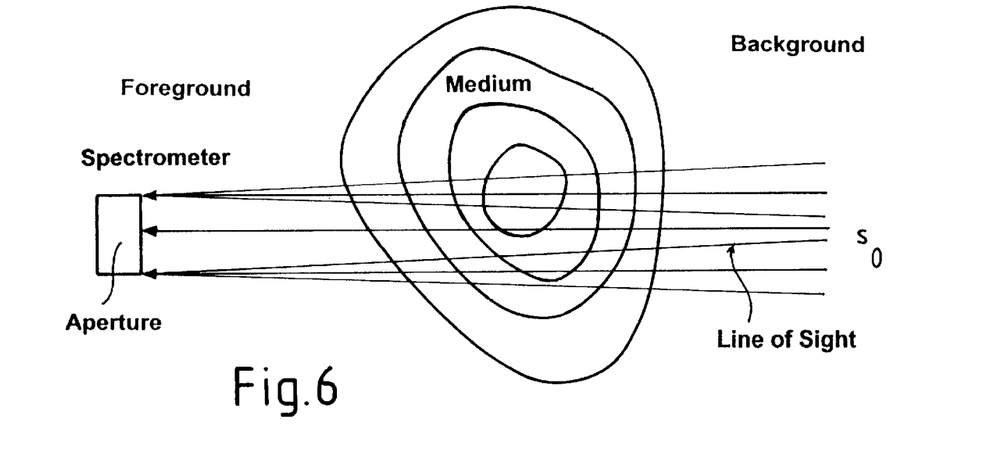
FIG. 6 is a schematic illustration of the geometry of the radiation transport at a finite FOV and aperture opening of the spectrometer.

During the modeling according to the invention of the observed radiation, the influence by the spectrometer is taken into account. Due to the finite aperture of the spectrometer optics (FOV or Field of View, in FIG. 5) it sees not only one single line of sight (or ray) but a beam of finite extent. This overlap of more than one line of sight means that the intensity is described with a folding integral according to $$I(v,s) = \int_{FOV} I(v,s,\alpha) FOV(\alpha) d\alpha \qquad (4)$$

wherein v is spectral wave number, s is the distance to the parcel of gas, and $I(v,s,\alpha)$ is the radiation entering at the angle $\alpha$ and the angle dependence is described with the function $FOV(\alpha)$, which is usually a box function. The integration in equation (4) utilizes a suitable Gaussian quadrature method, such as the Gauss-Legendre quadrature method with at least three lines of sight. Furthermore, because of the finite receiver aperture of the spectrometer, not only one beam of rays but a number of parallel beams need to be considered (as shown in FIG. 6), which is addressed analogously through integration via the aperture. (In the case of absorption measurements the modeling of the transmission (equation 2) needs to be modified analogously.)

To prevent the shortcomings associated with the Curtis-Godson approximation, the integration into the equations (1) and (2) is performed, according to the invention, with standard quadrature processes, for example Newton-Cotes formulas.

In the evaluation processes according to the invention, a number of spectra are evaluated simultaneously on one hand, and the modeling of the unknown profiles is improved on the other hand. With the measuring process according to the invention a number of spectra are measured, which are evaluated in the sense of a "global fit" in a least squares process. For this purpose the measurement vectors $g_s$ that correspond to the individual spectra are concatenated for $s=1, \ldots, S$ to a total vector $G=(g_1, \ldots, g_s)$ and the minimalization condition is applied to this vector:

$$\min_x \|G - Y(x)\|^2 = \min_x \sum_{s=1}^{S} \sum_{i=1}^{m} (g_{s,i} - y_s(v_i, x))^2. \qquad (5)$$

(The vector x designates the unknown parameters that need to be determined. In the present example spectra of equal lengths were assumed for reasons of simplicity. Thus, the vector Y(x) represents the observed radiation predicted from estimated values x of the gas parameters such as chemical component, temperature, etc.)

In the evaluation processes the inhomogeneous exhaust stream is approximated with a homogenous layer of constant conditions and characteristic values of this one layer model are determined, e.g., the mean temperature, CO, $CO_2$ or NO concentrations. A feature of the present invention is the determination of the spatial distribution of these parameters. Three methods according to the invention, which are described in more detail in the following paragraphs, are used for the discretization of the unknown source function:

Parameterization of the source function via a "simple" analytical expression;

Discretization through expansion according to a functions system;

Discretization via quadrature method.

The process according to the invention for the determination of concentration and temperature profiles from the measured radiance spectra is simplified in those cases in which additional information is available about the profiles. In practice there are cases, for example, in which it is known from knowledge of the chemical/physical processes during the propagation of the exhaust gases that the resulting profiles can be described with a certain class of functions.

One example is aircraft jet engines, that will be described in the following.

In jet engines the exhaust gas is emitted at a high speed. Intermixing with the ambient air is thus only gradual. The distribution process during the first few meters behind the nozzle thus depends primarily on the condition of the gas at the time of exit and can be described with analytical equations. Simulation programs exist, with which temperature and concentration profiles can be forecast based on the knowledge of the conditions in the exit plane.

Figure 7:
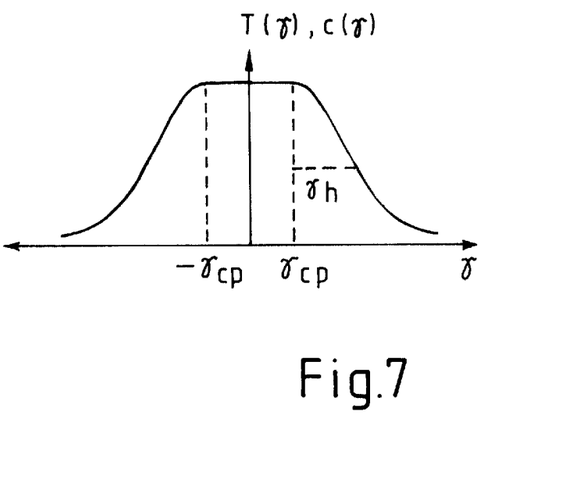
FIG. 7 is a radial profile for temperature and particle densities of the molecules.

Jet engines can be divided into categories that differ in the forms of their temperature and concentration profiles that appear during the first meters behind the nozzle. This is a known fact. The resulting profiles for civilian jet engines, for example, are radial profiles as shown in FIG. 7. As can be seen from the illustration of the radial profile in FIG. 7, the conditions are constant in the center (around r=0). This region decreases as the distance from the nozzle increases, until it disappears completely. In a similar manner the values decrease further towards the outside in accordance with a Gaussian function.

The radial profiles can be described analytically with the aid of equation (6)

$$f(r) = \begin{cases} f_{max} & \text{für } |r| < r_c \\ (f_{max} - f_{amb})\exp\left(-\frac{(|r|-r_c)^2}{r_h^2}\right) + f_{amb} & \text{für } |r| \geq r_c \end{cases} \quad (6)$$

wherein f denotes the exhaust gas temperature or the number density of the gases (number of molecules per volume unit). The indices 'max' and 'amb' designate the maximum values or the ambient conditions, respectively; r is the radius coordinate, with r=0 located in the center of the nozzle; $r_c$ is the radius up to which the gas characteristics are constant. For radii $r > r_c$, the profile decreases with the half value radius $r_h$ to ambient conditions in a Gaussian curve.

The parameters $r_c$ and $r_h$ are functions of the distance from the nozzle. $r_c$ becomes smaller as the distance increases and approaches zero. At the same time the half value width ($r_h$) increases. As a general rule, the geometry parameters ($r_c$ and $r_h$) furthermore depend on the quantity (temperature, species). The specific profiles may therefore differ depending on the observed species. However, a common profile can often be assumed at least in an approximation.

The measured radiance spectra are used to determine the parameters of the functional correlations of equation (6). This is done preferably simultaneously for all measurements with the aid of the Gaussian parameter estimation techniques (least squares fit).

The required parameters are first combined into a vector. For example, if it is assumed in a simplified manner that the ambient conditions are known and all profiles exhibit equal geometry parameters, the following results:

$$x = [r_c, r_h, T_{max}, c_{1,max}, c_{2,max}, \ldots, c_{N,max}] \quad (7)$$

wherein $T_{max}$ represents the maximum temperature and $c_{i,max}$ represents the maximum number density of the gas i. The vector x is now determined with the aid of known numeric algorithms (least squares data fitting).

In the previous paragraph the functional spatial of the temperature and gas concentration profiles was explicitly presupposed and the unknown profiles were parameterized with simple functions. For gas volumes of a largely unknown structure this restriction is dropped and the unknown profiles are expanded more generally according to a suitable set of functions.

In the one-dimensional case of cylindrical symmetry, the unknown profile is expanded into radially dependent functions:

$$f(r) = \sum_{j=1}^{n} x_j \Phi_j(r). \quad (8)$$

The required parameters are first combined into a vector. For example, if it is assumed in a simplified manner that the ambient conditions are known and all profiles exhibit equal geometry parameters, the following results:

$$x = [r_c, r_h, T_{max}, c_{1,max}, c_{2,max}, \ldots, c_{N,max}] \quad (7)$$

wherein $T_{max}$ represents the maximum temperature and $c_{i,max}$ represents the maximum number density of the gas i. The vector x is now determined with the aid of known numeric algorithms (least squares data fitting).

In the previous paragraph the functional spatial of the temperature and gas concentration profiles was explicitly presupposed and the unknown profiles were parameterized with simple functions. For gas volumes of a largely unknown structure this restriction is dropped and the unknown profiles are expanded more generally according to a suitable set of functions.

In the one-dimensional case of cylindrical symmetry, the unknown profile is expanded into radially dependent functions:

$$f(r) = \sum_{j=1}^{n} x_j \Phi_j(r). \quad (8)$$

wherein f(r) is the (temperature or gas) profile to be determined in dependence upon the distance to the symmetry axis, $\Phi_j$ is a suitably selected set of functions, e.g., linear splines, "hat functions" or the Eigen-functions of the harmonic oscillator ($\Phi_0(r) \sim \exp(-r^2)$, $\Phi_1(r) \sim r \exp(-r^2)$ ...), and $x_j$, j=1, . . . ,n are the n unknown expansion coefficients, which are determined within the meaning of the least squares according to equation (3) or (5). In the general case, in which a number of profiles need to be determined, each of these profiles is expanded and the vector x to be determined in the least squares method is given through the concatenation of the expansion coefficients of all profiles.

This expansion approach is also used for cases in which only one spectrum corresponding to a line of sight was measured; the radial coordinate must accordingly be replaced with the coordinate along the line of sight.

In the two-dimensional (or three-dimensional) case, the unknown profile function, in generalization of the one dimensional expansion of equation (8), is presented as the following sum $$f(\vec{r}') = \sum_{j=1}^{n} x_j \phi_j(\vec{r}') \quad (9)$$

wherein the n expansion coefficients $x_1, \ldots, x_n$ again are determined through minimalization of the residues norm (equations (3) or (5)). The expansion functions depending on the two space coordinates of the space vector, $\vec{r} = (x,y)$ are selected, for example, as product functions $$\phi(x,y) = \phi(x)\phi(y)$$

i.e., $$f(x, y) = \sum_{k,l} x_{kl} \phi_k(x) \phi_l(y) \quad (10)$$

The three-dimensional case is analogous.

Numeric quadrature methods are based on the substitution of an integral $$\int_a^b \phi(s) ds$$

with a sum $$\sum_{i=1}^{N} \omega_i \phi(s_i)$$

with the weights $\omega_i$ and nodes $s_i$ depending on the integration interval and on the selected numeric process. If a numeric integration of the $n^{th}$ degree is observed, the path integrals in equation (1) or (2) are approximated via:

$$g(v_i) = \sum_{j=1}^{n} w_j K(v_i; s_j) f(s_j) \quad \text{für } i = 1, 2, \ldots, m. \quad (11)$$

for i=1, 2, ... m and with $g_i=g(v_i)$, $A_{ij} \equiv \omega_j K(v_i, s_j)$ and $x_j \equiv f(s_j)$ a matrix equation is obtained:

$$g_i = \sum_{j=1}^{n} A_{ij} x_j \quad \text{oder} \quad g = Ax. \quad (12)$$

so that the values of the unknown profile function $x_j \equiv f(s_j)$ now are the n unknown parameters to be determined with the aid of the least squares method (3) or (5).

Figure 8:
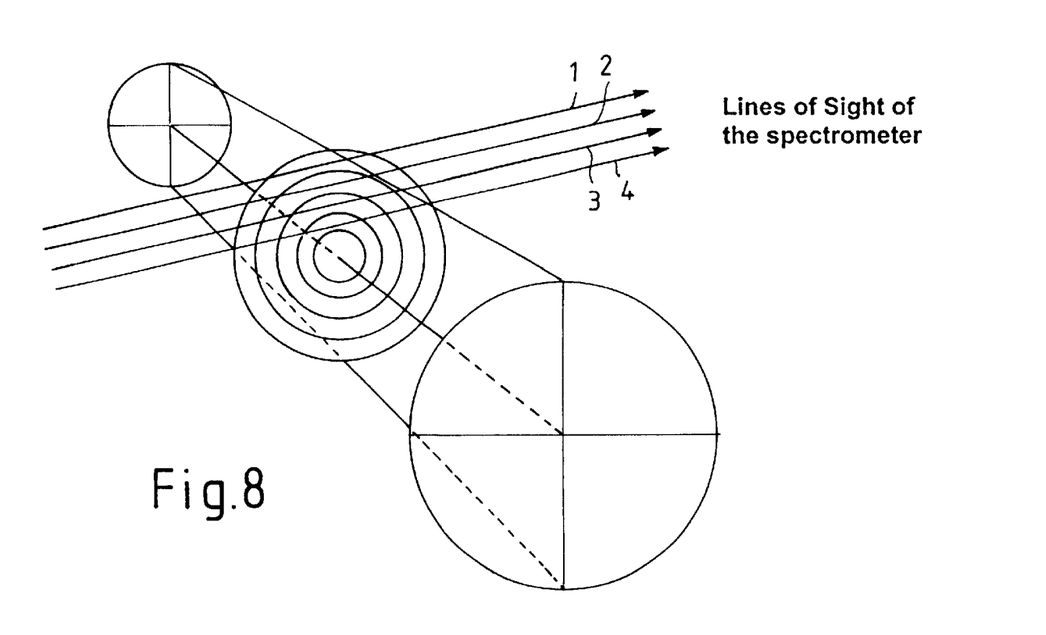
FIG. 8 is a schematic illustration of a sampling of a cylindrically symmetric medium.

If it can be assumed for the determination of concentration and temperature profiles from emission spectra that the medium to be examined is radially symmetric, as in the case of the exhaust stream, information regarding the shape of the profile is gained according to the invention through radial sampling according to FIG. 8.

For evaluation purposes, a small disk perpendicular to the symmetry axis of the medium (direction of extent of the exhaust steam) is observed and divided into r annuli. It is assumed that the temperature and concentration within an appropriately thin ring are constant. From the measured spectrum $g_1$, whose line of sight extends through the outermost ring, the corresponding condition parameters $x_1$ of the medium are then determined in this ring with the aid of a least squares method, $$\min_{x_1} \|g_1 - y_1(x_1)\|^2, \quad (13)$$

wherein $y_1(x_1)$ is the corresponding model for the description of the radiation transport through the ring and depends upon the parameters $x_1$. With these parameters $x_1$, which are now considered known, the parameters $x_2$ of this ring are now determined, also with a least squares method, from the spectrum $g_2$, whose line of sight extends through the outermost and the next inner ring. This process is now applied successively to each further inner ring until the symmetry axis of the medium has been reached, $$\min_{x_s} \|g_s - y_s(x_1, x_2, \ldots, x_{j-1}, x_j)\|^2 \quad \text{für } j = 1, \ldots, r. \quad (14)$$

In this manner all concentrations and temperatures are determined in dependence upon the distance to the symmetry axis of the medium. This sequential evaluation is easy to implement and permits a recursive determination of the layers. Alternatively, the individual spectra are combined into a total measurement vector $$G = (g_1^T, g_2^T, \ldots g_r^T)^T$$

in the sense of the above mentioned global fit method and the entirety of all parameters to be determined $$(\text{Vector } x = (x_1^T, x_2^T, \ldots x_r^T)^T$$

is fitted simultaneously.

Figure 9:
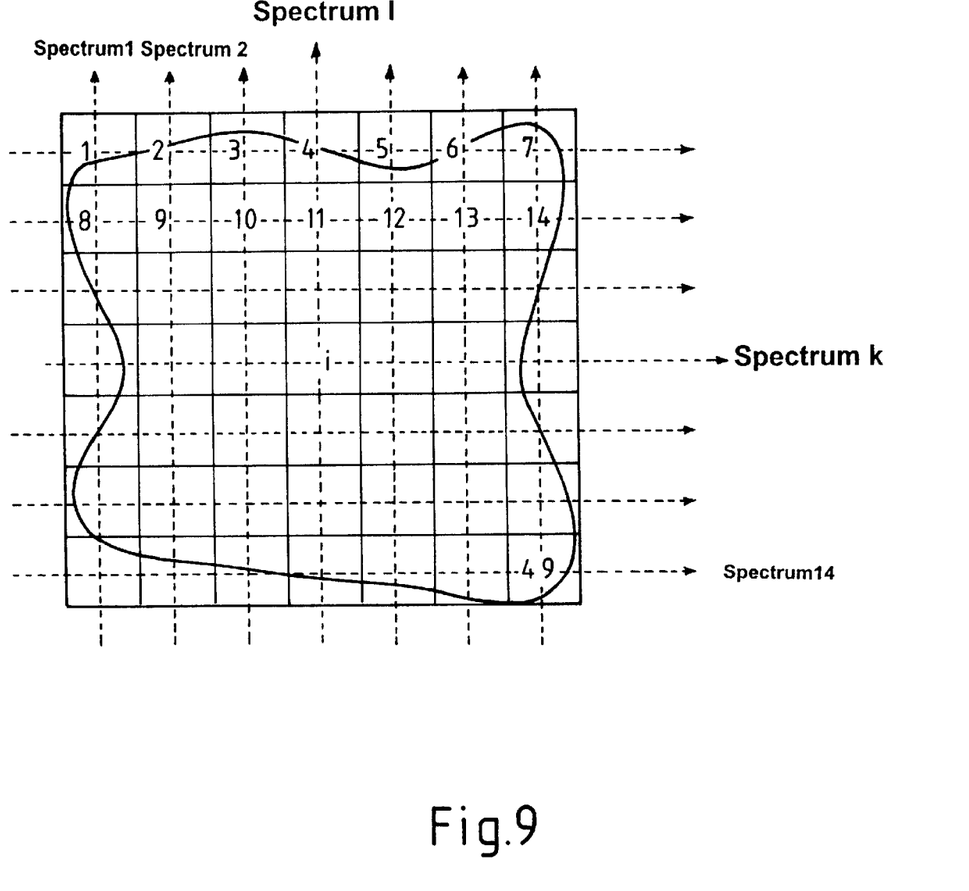
FIG. 9 is a schematic rendering of a sampling of a medium of a general shape.

If a cylindrical symmetry of the medium to be evaluated cannot be assumed for the determination of concentration and temperature profiles from emission spectra of a randomly shaped medium, the medium is observed from at least two directions to obtain spatial information on the shape of concentration and temperature profiles. FIG. 9 shows a simple set-up for the evaluation of the medium in which two perpendicular observation directions are observed. The illustration, again, shows a section through the medium.

The grid in FIG. 9 describes a division of the medium into ranges. The numbering of the ranges is arbitrary. Each range with the number i has a corresponding set of parameters $x_i$ to be determined. In the present example each of these ranges is observed from two perpendicular directions, i.e., to each range belong two spectra $g_k$ and $g_l$, in which information is contained regarding the parameters $x_i$. FIG. 9 showing an example of m=n=7; in this case both indices k and L would run from 1 to 7. If m spectra are measured in one direction and n spectra in the other direction, then $S_f$=m·n ranges are obtained (where "·" denotes ordinary multiplication) and altogether $S_g$=m+n spectra.

By combining the parameter vectors xi into a total vector $$X = (x_1^T, x_2^T, \ldots x_{s_f}^T)^T$$

and the spectra $g_k$ into a total measurement vector $$G = (g_1^T, g_2^T, \ldots g_{S_g}^T)^T$$

one again gets to the formulation of a least squares problem as in equation (5).

If the spatial resolution is increased by means of narrower sampling and/or the number of unknown values is increased (for example through a higher number of expansion coefficients in equation (8) or (9) or more quadrature points in equation (11)), the described least squares problems become ill-conditioned. This is based, on one hand, on the increasing overlaps of the line of sights of the spectrometer; spectra of adjacent lines of sight become more and more alike, thus tending to contain less and less new information. On the other hand, the required parameters in the case of a medium of general shape increases with the number of measured spectra according to the square-law.

In order to obtain the maximum information content and, hence, a higher spatial resolution despite ill-conditioning, so-called regularization processes are used in which additional information about the profiles is added into the least squares problem. Additional information of this type is entered through a constraint of smoothness conditions for the profiles or through a constraint of the monotony of the profiles in certain ranges.

With the regularization according to Phillips and Tikhonov, a smoothness constraint is entered into the least squares problem (equation (3) or (5)) in the form of a quadratic constraint $$\min_{x}(\|G - Y(x)\|^2 + \lambda^2 \|L(x - x_0)\|^2) \quad (15)$$

wherein L is a unit matrix or a matrix, which corresponds to the discrete representation of spatial derivative operators, $x_0$ is an a priori assumption regarding the required profiles, and $\lambda$ is the so-called regularization parameter, which determines the weight of the quadratic side constraint. In this manner not only the distance between measurement and model but, for example, also the norm (of the derivative) of the profiles is minimized. Effectively this corresponds to the requirement for the smoothness of the profile. If an a priori profile is not known, $x_0=0$ is applied.

Since the model $Y(x)$ is generally non-linear, the equation (15) is solved iteratively through linearization with, e.g., a Gauss-Newton method. For the selection of the regularization parameter $\lambda$ a series of methods exists, such as GCV, discrepancy principle, or the L-curve method.

According to the present process for quantitative analysis, especially of inhomogieneous gas volumes, spectrometers in the infrared, visible, or ultraviolet spectral range are used that are equipped with a device able to receive radiation of the observed gas volume from different directions having defined orientations towards each other (for example also perpendicular to each other). A number of spectra are measured, which are different from one another but linked to one another via the measuring geometry.

In the process according to the present invention this linkage is utilized through a corresponding linkage in the evaluation. The present model also contains the analytical description of a radiation transfer of the scene. With the aid of the evaluation the required gas parameters, such as spatial distribution of the concentrations and temperatures, are determined through comparison of the measured spectra with the modeled spectra and minimization of the squares of their differences.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means and materials for carrying out various disclosed functions may take a variety of alternative forms without departing from the invention.

Thus the expressions "means to . . . " and "means for . . . " as may be found in the specification above and/or in the claims below, followed by a functional statement, are intended to define and cover whatever structural, physical, chemical, or electrical element or structure may now or in the future exist which carries out the recited function, whether or not precisely equivalent to the embodiment or embodiments disclosed in the specification above; and it is intended that such expressions be given their broadest interpretation.

What is claimed is:

1. A process for quantitative analysis of at least one gas parameter over a volume of gas, the analysis being by emission or absorption spectrometry measuring a spectral transmission T or a spectral radiance (intensity) I within a field of view of the spectrometer; the process comprising:

providing a spectrometer measuring in the ultra-violet, visible or infrared spectral range and within an optical beam centered on an optical axis;

geometrically defining an observation plane oriented approximately perpendicular to a longitudinal gas volume axis;

in a first series of measurements, measuring m spectra with the optical axis of the spectrometer lying substantially within the observation plane, while shifting the optical axis within the observation plane between measurements of the m spectra;

in a second series of measurements, measuring n spectra with the optical axis of the spectrometer lying substantially within the observation plane, while shifting the optical axis within the observation plane between measurements of the n spectra;

whereby two orthogonal sets of optical beams intersect within the observation plane defining a spectrometer optical-axis grid including (m·n) beam-intersection partial volumes;

estimating parameter profiles within the gas volume by mathematically correlating the (m+n) measurements.

2. The process according to claim 1, wherein an orientation of the optical axis for the n spectra is substantially perpendicular to an orientation of the optical axis for the m spectra.

3. The process according to claim 1, including determining a beam-intersection partial volume size according to a solid angle of the optical axis of the spectrometer and a distance to the interface volume.

4. The process according to claim 1, wherein the step of shifting the optical axis within the observation plane between measurements of the m spectra includes shifting the optical axis laterally by a first distance, and the step of shifting the optical axis within the observation plane between measurements of the n spectra includes shifting the optical laterally by a second distance.

5. The process according to claim 1, wherein at least one of the steps of shifting the optical axis includes swivelling the optical axis, whereby the optical beams are fanned.

6. The process according to claim 1, comprising a step of reproducing an orientation of the optical axis of the spectrometer.

7. The process according to claim 1, wherein the spectrometer comprises a radiation emitter and an opposed radiation receiver receiving radiation from the radiation emitter, whereby the spectral transmission $\tau$ is measurable.

8. The process according to claim 1, wherein the step of shifting the optical axis within the observation plane comprises selecting one of a plurality of spectrometers.

9. The process according to claim 8, wherein each beam-intersection partial volume corresponds to a respective pair of the spectrometers.

10. The process according to claim 9, wherein the gas volume axis is a longitudinal axis of an exhaust stream of the gas.

11. The process according to claim 10, wherein the exhaust stream (22) comprises gas from a gas turbine, the observation plane is perpendicular to the longitudinal axis (210) of the exhaust stream (22), and the process comprises;

providing a spectrometer holding device (24) that encompasses the exhaust stream and is shiftable in a directions parallel and perpendicular to the longitudinal axis (210) of the exhaust stream;

wherein the plurality of spectrometers comprises a corresponding respective plurality of (m+n) optical receiver units (25) disposed and mounted on the holding device;

wherein a first subset of the receiver units comprises a number m of receiver units, a second subset of the receiver units comprises a number n of receiver units, wherein optical axes (211) of the first subset are substantially parallel to one another and are perpendicular to optical axes (211) of the second subset, and the optical axes (211) of the second subset are substantially parallel to one another;

whereby the two orthogonal sets of optical beams which intersect within the observation plane are formed by the first subset and the second subset, and rays received by the (m+n) receiver units (25) comprise the spectrometer optical-axis grid having (m·n) beam-intersection partial volumes, which is perpendicular to the longitudinal axis (210) of the exhaust stream (22); and wherein the plurality of spectrometers further comprise (m+n) fiber opticsibundles (26), each of the fiber optic bundles including a first end optically coupled to a respective one of the receiver units (25) and a second end optically coupled to an input of an optical multiplexer (27), and a spectrum analyzer (21) coupled to an output of the optical multiplexer (27).

12. The process according to claim 1, wherein the step of mathematically correlating over the gas volume comprises modeling the spectral transmission τ or the spectral radiance (intensity) I for each of the (m+n) lines of sight.

13. The process according to claim 1, wherein the spectrometer field of view includes a finite aperture, and wherein the step of mathematically correlating over the gas volume comprises taking into consideration the spectrometer field of view through a beam of rays of finite extent as an overlap of a number of lines of sight in the form of a convolution integral according to an equation $$I(v, s) = \int_{FOV} I(v, s, \alpha) FOV(\alpha) d\alpha, \text{ and} \quad (4)$$

integrating into the equation (4) through a Gauss-Legendre quadrature process with at least three lines of sight, whereby the process takes into consideration the finite aperture through several beams of rays that are shifted in a parallel direction in the form of an analogous integration via the aperture.

14. The process according to claim 1, comprising measuring at least one spectrum and determining therefrom via a least squares method a temperature or spatial density distribution of the exhaust gas components.

15. The process according to claim 14, comprising measuring a plurality of spectra, numbering s, each represented by a vector g and evaluating the spectra simultaneously, via the least squares method, by concatenating the measured vectors $g_s$ corresponding to each one of the plurality of spectra for s=1, 2, ... s into a total vector $G=(g_l \ldots g_s)$ and applying a minimalization condition to the total vector G.

16. The process according to claim 14, comprising parameterizing a source function via a simple analytical expression and, if analytically-describable additional information about profiles is available, then using measured radiation spectral intensity to determine parameters of functional correlations simultaneously for all measurements with the aid of the Gaussian adjustment of observations including a least squares fit, by combining required parameters into a vector and determining the vector with the aid of numeric algorithms including adjustment of observations;

whereby the modeling of unknown profiles is improved.

17. The process according to claim 1, comprising modeling the volume of gas, on the basis of a cylindrical symmetry, by (a) determining one-dimensional radially-dependent scalar functions of a gas parameter $$f(r) = \sum_{j=1}^{n} x_j \Phi_j(r). \quad (8)$$

wherein f(r) is a radial profile function of the parameter, $\Phi_j$ denotes a family of functions, and $X_j$ (with j=1, ..., n) are n expansion coefficients determined according to $$\min_x \|g - y(x)\|^2 = \min_x \sum_{i=1}^{m} (g_i - y(v_i, x))^2 \quad (3)$$

or $$\min_x \|G - Y(x)\|^2 = \min_x \sum_{s=1}^{S} \sum_{i=1}^{m} (g_{s,i} - y_s(v_i, x))^2 \quad (5)$$

(b) representing the gas two-dimensionally or three dimensionally as a vector $$f(\vec{r}) = \sum_{j=1}^{n} x_j \Phi_j(\vec{r}) \quad (9)$$

where r=(x,y) and x or y are spatial components of the vector, and wherein a value of the parameter at (x,y) comprises product functions ø(x,y)=ø(x) ø(y), such that $$f(x, y) = \sum_{k,l} x_{kl} \phi_k(x) \phi_l(y). \quad (10)$$

18. The process according to claim 17, wherein the $\phi_j$ family of functions includes at least one of linear splines, hat functions, or characteristic functions of the harmonic oscillator $\phi_0$ (r) ~exp ($-r^2$), $\phi_1$ (r) ~r exp ($-r^2$), ...

19. The process according to claim 14, comprising a step of discretizing through quadrature methods to improve modeling of gas-parameter profiles.

20. The process according to claim 15, wherein for gas volumes of a largely unknown structure the process includes expanding each gas parameter profile required for modeling the gas according to a selected set of functions, and determining the vector x via concatenation of expansion coefficients of all profiles as determined by a least squares method.

21. The process according claim 1, wherein, in case no information is available about the gas parameter profiles, the process includes observing the gas volume from at least two directions within the observation plane to obtain spatial information on concentration or temperature profiles, whereby the spectrometer optical-axis grid divides the gas volume into ranges, with a set of parameters belonging to each range;

concatenating together the parameters into a total parameter vector;

analogously concatenating together the measured spectra into a total measured vector; and solving a resulting least squares problem according to global fit method.

22. The process according to claim 1, comprising determining concentration or temperature parameter profiles from emission spectra of a cylindrically symmetric gas medium;

radially measuring to obtain information on a course of a profile; and evaluating sequentially from the outside in.

23. The process according to claim 1, comprising, in a case in which measured spectra lead to ill-conditioned least squares problems because of overlapping lines of sight, obtaining the maximum information and improved spatial resolution from the measured spectra by applying regularization techniques that impose additional constraints, e.g. profile smoothness or profile monotonicity within certain ranges, and entering the maximum information into a least squares problem by adding a priori knowledge of the shape of the profiles.

24. The process according to claim 1, comprising a step of shifting the observation plane, in which the (m+n) spectral measurements are performed, in a direction perpendicular to the observation plane.

* * * * *